United States Patent
Nielsen et al.

(10) Patent No.: US 9,522,238 B2
(45) Date of Patent: Dec. 20, 2016

(54) INJECTION DEVICE COMPRISING AN OPTICAL SENSOR

(71) Applicant: Novo Nordisk A/S, Bagsvaerd (DK)

(72) Inventors: Preben M. Nielsen, Holbaek (DK);
Bodo von Munchow, Lyngby (DK);
Carsten B. Pedersen, Holstebro (DK);
Per M. Pedersen, Struer (DK)

(73) Assignee: Novo Nordisk A/S, Bagsvaerd (DK)

( * ) Notice: Subject to any disclaimer, the term of this patent is extended or adjusted under 35 U.S.C. 154(b) by 283 days.

(21) Appl. No.: 14/292,063

(22) Filed: May 30, 2014

(65) Prior Publication Data

US 2014/0276381 A1    Sep. 18, 2014

Related U.S. Application Data

(62) Division of application No. 13/461,415, filed on May 1, 2012, now Pat. No. 8,771,238, which is a division of
(Continued)

(30) Foreign Application Priority Data

May 10, 2005    (EP) .................................. 05010109

(51) Int. Cl.
*A61M 5/178*    (2006.01)
*A61M 5/315*    (2006.01)
*G01D 5/347*    (2006.01)

(52) U.S. Cl.
CPC ....... *A61M 5/31525* (2013.01); *A61M 5/3155* (2013.01); *A61M 5/31556* (2013.01);
(Continued)

(58) Field of Classification Search
CPC ............. A61M 2205/3306; A61M 2205/6063; A61M 5/31525; A61M 5/3155
See application file for complete search history.

(56) References Cited

U.S. PATENT DOCUMENTS 3,700,862 A    10/1972    Snook et al.
3,809,863 A    5/1974    Oberg
(Continued)

FOREIGN PATENT DOCUMENTS

CN    1051152 A    5/1991
CN    1013704    8/1991
(Continued)

OTHER PUBLICATIONS

International Search Report for PCT/EP07/054069, mailed Sep. 17, 2007.
(Continued)

*Primary Examiner* — Aarti B Berdichevsky
(74) *Attorney, Agent, or Firm* — Wesley Nicolas (57) ABSTRACT

The present invention relates to an injection device comprising an optically-based sensor for determining the position or setting of a dose setting member arranged to set a dose to be injected from the injection device. In particular, the present invention relates to an injection device comprising a rotatably mounted member having a plurality of optically coded paths arranged on an outer surface thereof. The rotatably mounted member is operatively connected to the dose setting member and is adapted to rotate with the dose setting member.

18 Claims, 4 Drawing Sheets

Related U.S. Application Data application No. 11/912,347, filed as application No. PCT/EP2006/062133 on May 8, 2006, now Pat. No. 8,197,449.

(60) Provisional application No. 60/684,321, filed on May 25, 2005.

(52) U.S. Cl.
CPC . *A61M 5/31568* (2013.01); *A61M 2205/3306* (2013.01); *A61M 2205/6063* (2013.01); *G01D 5/3473* (2013.01); *G01D 5/34792* (2013.01)

(56) References Cited

U.S. PATENT DOCUMENTS

| | | |
|---|---|---|
| 3,916,157 A | 10/1975 | Roulette et al. |
| 3,998,513 A | 12/1976 | Kobayashi et al. |
| 4,179,212 A | 12/1979 | Lahr |
| 4,327,283 A | 4/1982 | Heyman et al. |
| 4,355,300 A | 10/1982 | Weber |
| 4,420,754 A | 12/1983 | Andermo |
| 4,449,042 A | 5/1984 | Hampson et al. |
| 4,476,149 A | 10/1984 | Poppe et al. |
| 4,476,381 A | 10/1984 | Rubin |
| 4,591,707 A | 5/1986 | Stenzel et al. |
| 4,625,101 A | 11/1986 | Hinks et al. |
| 4,636,786 A | 1/1987 | Haertling |
| 4,693,574 A | 9/1987 | Ohnuki et al. |
| 4,731,526 A | 3/1988 | Knoll et al. |
| 4,739,377 A | 4/1988 | Allen |
| 4,764,767 A | 8/1988 | Ichikawa et al. |
| 4,810,867 A | 3/1989 | Speicher |
| 4,850,966 A | 7/1989 | Grau et al. |
| 4,853,521 A | 8/1989 | Claeys et al. |
| 4,857,716 A | 8/1989 | Gombrich et al. |
| 4,880,014 A | 11/1989 | Zarowitz et al. |
| 4,896,946 A | 1/1990 | Suzuki et al. |
| 4,930,263 A | 6/1990 | Rando |
| 4,950,246 A | 8/1990 | Muller |
| 4,959,056 A | 9/1990 | Dombrowski et al. |
| 4,978,335 A | 12/1990 | Arthur, III |
| 5,059,776 A | 10/1991 | Antes |
| 5,077,635 A | 12/1991 | Bollhagen et al. |
| 5,078,683 A | 1/1992 | Sancoff et al. |
| 5,091,798 A | 2/1992 | Hibino |
| 5,132,026 A | 7/1992 | Baluyot et al. |
| 5,153,827 A | 10/1992 | Coutre et al. |
| 5,174,766 A | 12/1992 | Yoshizawa et al. |
| 5,176,502 A | 1/1993 | Sanderson et al. |
| 5,196,683 A | 3/1993 | Marom et al. |
| 5,239,307 A | 8/1993 | Andermo |
| 5,271,527 A | 12/1993 | Haber et al. |
| 5,305,147 A | 4/1994 | Hasegawa et al. |
| 5,311,364 A | 5/1994 | Kanoshima et al. |
| 5,317,506 A | 5/1994 | Coutre et al. |
| 5,336,871 A | 8/1994 | Colgate, Jr. |
| 5,379,131 A | 1/1995 | Yamazaki |
| 5,394,206 A | 2/1995 | Cocca |
| 5,403,616 A | 4/1995 | Hattori et al. |
| 5,418,649 A | 5/1995 | Igarashi |
| 5,422,472 A | 6/1995 | Tavislan et al. |
| 5,430,278 A | 7/1995 | Krieg et al. |
| 5,432,329 A | 7/1995 | Colgate, Jr. et al. |
| 5,461,239 A | 10/1995 | Atherton |
| 5,523,560 A | 6/1996 | Manique et al. |
| 5,569,212 A | 10/1996 | Brown |
| 5,585,615 A | 12/1996 | Iwanami et al. |
| 5,593,390 A | 1/1997 | Castellano et al. |
| 5,628,309 A | 5/1997 | Brown |
| 5,637,854 A | 6/1997 | Thomas |
| 5,643,212 A | 7/1997 | Coutre et al. |
| 5,675,380 A | 10/1997 | Florent et al. |
| 5,686,725 A | 11/1997 | Maruyama et al. |
| 5,747,350 A | 5/1998 | Sattler |
| 5,757,521 A | 5/1998 | Walters et al. |
| 5,764,457 A | 6/1998 | Uhde et al. |
| 5,777,303 A | 7/1998 | Berney |
| 5,782,814 A | 7/1998 | Brown et al. |
| 5,786,584 A | 7/1998 | Button et al. |
| 5,791,880 A | 8/1998 | Wilson |
| 5,792,117 A | 8/1998 | Brown |
| 5,793,502 A | 8/1998 | Bianco et al. |
| 5,821,521 A | 10/1998 | Bridgelall et al. |
| 5,821,524 A | 10/1998 | Horlbeck et al. |
| 5,876,380 A | 3/1999 | Manganini et al. |
| 5,880,683 A | 3/1999 | Brandestini |
| 5,882,463 A | 3/1999 | Tompkin et al. |
| 5,895,369 A | 4/1999 | Flower |
| 5,902,990 A | 5/1999 | Stewart |
| 5,925,867 A | 7/1999 | Hagimoto |
| 5,954,700 A | 9/1999 | Kovelman |
| 5,986,585 A | 11/1999 | Pusch |
| 6,003,775 A | 12/1999 | Ackley |
| 6,019,745 A | 2/2000 | Gray |
| 6,047,892 A | 4/2000 | Schuessler et al. |
| 6,053,415 A | 4/2000 | Norwood |
| 6,068,615 A | 5/2000 | Brown et al. |
| 6,090,064 A | 7/2000 | Reilly et al. |
| 6,110,148 A | 8/2000 | Brown et al. |
| 6,110,152 A | 8/2000 | Kovelman |
| 6,168,080 B1 | 1/2001 | Verschuur et al. |
| 6,177,683 B1 | 1/2001 | Kolesar et al. |
| 6,202,929 B1 | 3/2001 | Verschuur et al. |
| 6,215,508 B1 | 4/2001 | Bryan et al. |
| 6,265,466 B1 | 7/2001 | Glatkowski et al. |
| 6,274,092 B1 | 8/2001 | Itoh |
| 6,303,929 B1 | 10/2001 | Oshima et al. |
| 6,329,813 B1 | 12/2001 | Andermo |
| 6,352,523 B1 | 3/2002 | Brown et al. |
| 6,372,293 B1 | 4/2002 | Mathus et al. |
| 6,435,175 B1 | 8/2002 | Stenzler |
| 6,475,192 B1 | 11/2002 | Reilly et al. |
| 6,482,185 B1 | 11/2002 | Hartmann |
| 6,533,183 B2 | 3/2003 | Aasmul et al. |
| 6,598,796 B2 | 7/2003 | Harrop |
| 6,652,812 B1 | 11/2003 | Vartiainen et al. |
| 6,669,090 B2 | 12/2003 | Eilersen |
| 6,700,391 B2 | 3/2004 | Strack et al. |
| 6,813,868 B2 | 11/2004 | Baldwin et al. |
| 6,854,653 B2 | 2/2005 | Eilersen |
| 6,954,700 B2 | 10/2005 | Higashida et al. |
| 6,957,522 B2 | 10/2005 | Baldwin et al. |
| 6,976,349 B2 | 12/2005 | Baldwin et al. |
| 6,994,261 B2 | 2/2006 | Eilersen |
| 7,018,363 B2 | 3/2006 | Cowan et al. |
| 7,041,941 B2 | 5/2006 | Faries, Jr. et al. |
| 7,061,831 B2 | 6/2006 | De La Huerga |
| 7,074,209 B2 | 7/2006 | Evans et al. |
| 7,077,332 B2 | 7/2006 | Verschuur et al. |
| 7,104,973 B2 | 9/2006 | Woolston et al. |
| 7,108,184 B2 | 9/2006 | Mase et al. |
| 7,164,133 B2 | 1/2007 | Hjertman et al. |
| 7,462,166 B2 | 12/2008 | Cowan et al. |
| 7,511,480 B2 | 3/2009 | Steffen |
| 7,704,231 B2 | 4/2010 | Pongpairochana et al. |
| 8,140,349 B2 | 3/2012 | Hanson et al. |
| 2001/0001472 A1 | 5/2001 | Sano et al. |
| 2001/0013544 A1 | 8/2001 | Rathus et al. |
| 2001/0015202 A1 | 8/2001 | Miller |
| 2001/0034506 A1 | 10/2001 | Hirschman et al. |
| 2002/0000471 A1 | 1/2002 | Aasmul et al. |
| 2002/0012176 A1 | 1/2002 | Ning |
| 2002/0020654 A1 | 2/2002 | Eilersen |
| 2002/0022821 A1 | 2/2002 | Eilersen |
| 2002/0063156 A1 | 5/2002 | Marchand |
| 2002/0106309 A1 | 8/2002 | Mathus et al. |
| 2002/0117549 A1 | 8/2002 | Lee |
| 2002/0117579 A1 | 8/2002 | Kotoulas et al. |
| 2002/0123078 A1 | 9/2002 | Seul et al. |
| 2002/0177237 A1 | 11/2002 | Shvets et al. |
| 2003/0015590 A1 | 1/2003 | Chen |
| 2003/0034439 A1 | 2/2003 | Reime et al. |
| 2003/0039590 A1 | 2/2003 | Lodge |

(56) References Cited

U.S. PATENT DOCUMENTS

| | | |
|---|---|---|
| 2003/0116630 A1 | 6/2003 | Carey et al. |
| 2003/0143614 A1 | 7/2003 | Drmanac |
| 2003/0205625 A1 | 11/2003 | Eilersen |
| 2003/0233041 A1 | 12/2003 | Yaksh et al. |
| 2003/0233069 A1 | 12/2003 | Gillespie et al. |
| 2004/0008853 A1 | 1/2004 | Pelrine et al. |
| 2004/0024368 A1 | 2/2004 | Broselow |
| 2004/0046032 A1 | 3/2004 | Urano et al. |
| 2004/0051368 A1 | 3/2004 | Caputo et al. |
| 2004/0082918 A1 | 4/2004 | Evans et al. |
| 2004/0141426 A1 | 7/2004 | Kawasaki et al. |
| 2004/0155113 A1 | 8/2004 | Urano et al. |
| 2004/0178255 A1 | 9/2004 | Eich et al. |
| 2004/0200558 A1 | 10/2004 | Stevens et al. |
| 2004/0207385 A1 | 10/2004 | Gafner et al. |
| 2004/0210199 A1 | 10/2004 | Atterbury et al. |
| 2005/0006472 A1 | 1/2005 | Verschuur et al. |
| 2005/0035207 A1 | 2/2005 | Philyaw et al. |
| 2005/0060059 A1 | 3/2005 | Klein et al. |
| 2005/0116033 A1 | 6/2005 | Moore |
| 2005/0156318 A1 | 7/2005 | Douglas |
| 2005/0182360 A1 | 8/2005 | Yeandel et al. |
| 2005/0236603 A1 | 10/2005 | Faris |
| 2005/0283116 A1 | 12/2005 | Eakins et al. |
| 2006/0097877 A1 | 5/2006 | Baba et al. |
| 2006/0118612 A1 | 6/2006 | Christoffersen et al. |
| 2006/0125491 A1 | 6/2006 | Grishin et al. |
| 2006/0129104 A1 | 6/2006 | Cowan et al. |
| 2006/0138233 A1 | 6/2006 | Kemppainen et al. |
| 2006/0164002 A1 | 7/2006 | O'Brien et al. |
| 2006/0170981 A1 | 8/2006 | Ricks et al. |
| 2006/0175427 A1 | 8/2006 | Jonientz et al. |
| 2006/0176267 A1 | 8/2006 | Honeyman et al. |
| 2006/0224123 A1 | 10/2006 | Friedli et al. |
| 2006/0226238 A1 | 10/2006 | Salib et al. |
| 2006/0243804 A1 | 11/2006 | Christoffersen et al. |
| 2007/0080234 A1 | 4/2007 | Domoy |
| 2007/0239116 A1 | 10/2007 | Follman et al. |
| 2008/0015510 A1 | 1/2008 | Sandoz et al. |
| 2008/0269664 A1 | 10/2008 | Trovato et al. |
| 2009/0088701 A1 | 4/2009 | Larsen |

FOREIGN PATENT DOCUMENTS

| | | |
|---|---|---|
| DE | 1950411 A1 | 4/1971 |
| DE | 2636634 A1 | 2/1978 |
| DE | 3712089 A1 | 10/1988 |
| DE | 4234016 A1 | 4/1993 |
| DE | 4402319 A1 | 8/1994 |
| DE | 19504111 A1 | 8/1995 |
| DE | 19637967 A1 | 10/1997 |
| DE | 19814687 C1 | 2/1999 |
| DE | 10035192 C1 | 10/2001 |
| EP | 235691 A2 | 9/1987 |
| EP | 248165 A2 | 12/1987 |
| EP | 336778 A2 | 10/1989 |
| EP | 364010 A2 | 4/1990 |
| EP | 398717 A2 | 11/1990 |
| EP | 402553 A1 | 12/1990 |
| EP | 492954 A2 | 7/1992 |
| EP | 573129 A2 | 12/1993 |
| EP | 588427 A2 | 3/1994 |
| EP | 626660 A2 | 11/1994 |
| EP | 685810 A1 | 12/1995 |
| EP | 690457 A2 | 1/1996 |
| EP | 716290 A2 | 6/1996 |
| EP | 833273 A2 | 4/1998 |
| EP | 833278 A2 | 4/1998 |
| EP | 911859 A1 | 4/1999 |
| EP | 1095668 A1 | 5/2001 |
| EP | 1142643 A2 | 10/2001 |
| EP | 1143643 A2 | 10/2001 |
| EP | 1193641 A2 | 4/2002 |
| EP | 1246127 A2 | 10/2002 |
| EP | 1462134 A1 | 9/2004 |
| EP | 1503185 A2 | 2/2005 |
| FR | 2771111 A1 | 5/1999 |
| GB | 2088163 A | 6/1982 |
| GB | 2159007 A | 11/1985 |
| GB | 2216259 A | 10/1989 |
| GB | 2287551 A | 9/1995 |
| GB | 2309801 A | 8/1997 |
| GB | 2336927 A | 11/1999 |
| GB | 2341965 A | 3/2000 |
| JP | 56-094475 A | 7/1981 |
| JP | 59-131917 A | 7/1984 |
| JP | 63-100303 A | 5/1988 |
| JP | 2-085370 A | 3/1990 |
| JP | 2-188702 A | 7/1990 |
| JP | 2-250083 A | 10/1990 |
| JP | 3-027037 A | 2/1991 |
| JP | 4-222084 A | 8/1992 |
| JP | 4-233624 A | 8/1992 |
| JP | 4-233680 A | 8/1992 |
| JP | 4-233684 A | 8/1992 |
| JP | H04231804 | 8/1992 |
| JP | 5006449 A | 1/1993 |
| JP | 5-500917 | 2/1993 |
| JP | 5-314296 A | 11/1993 |
| JP | 6-163027 A | 6/1994 |
| JP | 06-171194 A | 6/1994 |
| JP | 6-333102 A | 12/1994 |
| JP | 7-098752 A | 4/1995 |
| JP | 7-271890 A | 10/1995 |
| JP | 8-106648 A | 4/1996 |
| JP | 8-118864 A | 5/1996 |
| JP | 8-179475 A | 7/1996 |
| JP | 8-220994 A | 8/1996 |
| JP | 8-262980 A | 10/1996 |
| JP | 9-016703 A | 1/1997 |
| JP | 9-034361 A | 2/1997 |
| JP | 9-091364 A | 4/1997 |
| JP | 9-192220 A | 7/1997 |
| JP | 9-223181 A | 8/1997 |
| JP | 9-274637 A | 10/1997 |
| JP | 10-105635 A | 4/1998 |
| JP | 10-268777 A | 10/1998 |
| JP | 11-135172 A | 5/1999 |
| JP | 11-162591 A | 6/1999 |
| JP | 11-180079 A | 7/1999 |
| JP | 11-276583 A | 10/1999 |
| JP | 11-316877 A | 11/1999 |
| JP | 2000-040119 A | 2/2000 |
| JP | 2000-272191 A | 10/2000 |
| JP | 2001-043301 A | 2/2001 |
| JP | 2001-075480 A | 3/2001 |
| JP | 2002-082120 A | 3/2002 |
| JP | 2002-517737 A | 6/2002 |
| JP | 2004-535590 A | 11/2004 |
| SU | 391384 A1 | 7/1973 |
| WO | 91/04759 A1 | 4/1991 |
| WO | 92/17231 A1 | 10/1992 |
| WO | 93/12828 A1 | 7/1993 |
| WO | 94/08647 A1 | 4/1994 |
| WO | 94/12235 A1 | 6/1994 |
| WO | 94/15120 A1 | 7/1994 |
| WO | 95/24317 A1 | 9/1995 |
| WO | 95/28190 A1 | 10/1995 |
| WO | 99/60533 A1 | 11/1999 |
| WO | 9965548 A1 | 12/1999 |
| WO | 00/42678 A1 | 7/2000 |
| WO | 01/22348 A1 | 3/2001 |
| WO | 01/54055 A1 | 7/2001 |
| WO | 01/62322 A1 | 8/2001 |
| WO | 01/70304 A1 | 9/2001 |
| WO | 01/84542 A2 | 11/2001 |
| WO | 0195959 A1 | 12/2001 |
| WO | 02/11792 A1 | 2/2002 |
| WO | 02/13133 A1 | 2/2002 |
| WO | 02/092153 A2 | 11/2002 |
| WO | 02/095675 A1 | 11/2002 |
| WO | 03009461 A1 | 1/2003 |
| WO | 03/011370 A2 | 2/2003 |
| WO | 03/011372 A2 | 2/2003 |

(56) References Cited

FOREIGN PATENT DOCUMENTS

| WO | 03/011373 A1 | 2/2003 |
|---|---|---|
| WO | 03/011374 A1 | 2/2003 |
| WO | 03011371 A2 | 2/2003 |
| WO | 03/017915 A1 | 3/2003 |
| WO | 03/020598 A2 | 3/2003 |
| WO | 03/038738 A1 | 5/2003 |
| WO | 03103753 A1 | 12/2003 |
| WO | 2004/084795 A1 | 10/2004 |
| WO | 2004/097715 A1 | 11/2004 |
| WO | 2005/004955 A1 | 1/2005 |
| WO | 2005/075010 A1 | 8/2005 |
| WO | 2005/089835 A1 | 9/2005 |
| WO | 2005/110387 A2 | 11/2005 |
| WO | 2006/113521 A2 | 10/2006 |
| WO | 2006/120182 A1 | 11/2006 |
| WO | 2007/039148 A1 | 4/2007 |
| WO | 2007/107562 A2 | 9/2007 |
| WO | 2007/116090 A1 | 10/2007 |
| WO | 2007/122253 A1 | 11/2007 |
| WO | 2009/015933 A1 | 2/2009 |

OTHER PUBLICATIONS

International Search Report for PCT/EP07/053558, mailed Jul. 13, 2007.
International Search Report for PCT/EP06/009240, mailed Jan. 4, 2007.

Coded paths

Fig. 6

INJECTION DEVICE COMPRISING AN OPTICAL SENSOR

CROSS-REFERENCE TO RELATED APPLICATIONS

This application is a Divisional of U.S. application Ser. No. 13/461,415, filed May 1, 2012, which is a Divisional of U.S. application Ser. No. 11/912,347, filed Jun. 27, 2008 (now U.S. Pat. No. 8,197,449, issued Jun. 12, 2012) which is a 35 U.S.C. §371 National Stage application of International Application PCT/EP2006/062133 (published as WO 2006/120182), filed May 8, 2006, which claimed priority of European Patent Application 05010109.6, filed May 10, 2005; this application claims priority under 35 U.S.C. §119 of U.S. Provisional Application 60/684,321; filed May 25, 2005, the contents of which are incorporated herein by reference.

The present invention relates to an injection device comprising an optically-based sensor for determining the position or setting of a dose setting member arranged to set a dose to be injected from the injection device. In particular, the present invention relates to an injection device comprising a rotatably mounted member having a plurality of optically coded paths arranged on an outer surface thereof.

BACKGROUND OF THE INVENTION

WO 2005/004955 disclosed a pen-like injection device for administering a fluid product. The device comprises an apparatus for contactless measurement of a position between at least two elements that are movable relative to each other. The measurement apparatus encompasses at least two optical sensors that are placed across from each other in a stationary manner on at least one first element and a second element which is movable relative to said at least one first element. A surface profile is provided on the second element, said surface profile supplying a different predetermined profile pattern for each of the optical sensors when the first element and the second element are moved relative to each other.

Thus, according to the method suggested in WO 2005/004955 the optical sensors record different predetermined profile patterns along the surface profile when the first element is moved relative to the second element. The recorded data from the optical sensors are jointly processed in order to determine the relative position between the elements.

Thus, the apparatus for contactless measurements suggested in WO 2005/004955 applies the recoding of different predetermined profile patterns in order to determine the relative position of the two elements. The use of profiles makes the apparatus and method suggested in WO 2005/004955 rather complicated in that such profiles increase the dimensions, especially the diameter, of the pen-like device.

It is an objection of the present invention to provide an optically-based read-out mechanism for determining the position, relative or absolute position, of a dose setting member in a pen-like injection device.

SUMMARY OF THE INVENTION

The above-mentioned object is complied with by providing, in a first aspect, an injection device comprising a dose setting member adapted to set a dose of a medicament to be injected from the injection device, the injection device further comprising a rotatably mounted member having a plurality of optically coded paths arranged on an outer surface thereof. The rotatably mounted member may be operatively connected to the dose setting member and is adapted to rotate with the dose setting member.

Within the context of this application, an optical coded path is defined as a circular or helical shaped track defining a series of information elements spanning the length of the optical coded path. A plurality of optical coded paths may be arranged parallel to each other, thereby defining a matrix representing a two-dimensional matrix of information elements consisting of rows and columns. The optical coded paths may be arranged so as to adjoin neighbouring optical coded paths.

The optically coded paths may be provided by varying the optical properties along said paths, such as by varying the optical reflectivity or transparency of the outer surface of the rotatably mounted member. The optical reflectivity or transparency may be varied along the path by positioning strips of metal foil on the outer surface of the rotatably mounted member. Alternatively, the optically coding of the paths may be provided by printing non-reflecting regions on a piece of reflecting tape or other sticky material.

Preferably, six optically coded paths are arranged on the outer surface of the rotatably mounted member. Having six optically coded paths allows the angular resolution to be 1/64. Thus, the dose setting member can be positioned at 64 positions within one revolution of the dose setting member.

Alternatively, the six optically coded paths are arranged along a helically extending track around the rotatably mounted member. Thus, the six optically coded paths allows the matrix of information elements span the total length of a helically extending track. In some variants, the helical extending track extends less than 360 degrees around the rotatably mounted member. However, in preferred embodiments, the matrix of information elements extends along the helical track around more than one complete revolution of the rotatably mounted member. Having six optically coded paths, the information elements permits 64 distinct codes to be covered by the entire matrix. If a particular pen design permits the rotatably mounted member to be rotated in discrete steps of 15 degrees, and the pen design permits a total of 64 distinct allowed positions, then the matrix may be arranged to extend approximately 2.6 revolutions around the rotatably mounted member. Thus an absolute sensing scheme can be obtained, where each code corresponds exactly to one of the 64 discrete rotational positions that the rotatably mounted member may experience.

In a first embodiment of the first aspect of the present invention, the injection device may further comprise means for guiding a plurality of light beams, each light beam being guided so as to be incident on one optically coded path. Preferably, the number of guided light beams equals the number of optically coded paths. The plurality of light beams may be generated from a single light source, such as a LED or a laser diode. The light source may emit light in the visible or near infrared region. In order to provide a plurality of light beams the light emitted from the single lights source may be guided into separate channels which guide each of the beams towards an optically coded path.

The injection device may further comprise light detecting means having a plurality of light sensitive elements or areas. Preferably, the number of light sensitive elements or areas equals the number of optically coded paths. In order to guide light to the light sensitive elements the injection device may further comprise means for guiding a plurality of light beams reflected from the optically coded paths to the light sensitive elements. These light guiding means may be arranged as through-going holes/openings or channels in a housing.

The light guiding means for guiding light to the optically coded paths may be arranged so that the light beams are incident onto the optically coded paths under an angle of incidence in the range 40-50 degrees, such as under approximately 45 degrees. Similarly, the light guiding means for guiding light from the optically coded paths to the light sensitive elements may be arranged so that the light beams leave the optically coded paths under an angle of 40-50 degrees, such as under approximately 45 degrees.

In further aspects of the invention, the coding of the matrix elements may be arranged to define a Gray code coding scheme or a Johnson code coding scheme.

In a second embodiment of the first aspect of the present invention 13, the rotatably mounted member may be at least partly transparent. This embodiment of the aspect of the present invention may further comprise light emitting means adapted to couple a beam of light into the rotatably mounted member. This light emitting means may be a LED or a laser diode emitting light in the visible or in the near infrared region. Light detecting means having a plurality of light sensitive areas may also be included. The light detecting means may be arranged to detect light escaping the outer surface of the rotatably mounted member where the optically coded paths are arranged. Thus, the information applied in determining the position or setting of the dose setting member is based on light escaping the at least partly transparent rotatably mounted member which is operatively connected to the dose setting member. Preferably, the number of light sensitive areas equals the number of optically coded paths. Furthermore, the light sensitive areas are preferably arranged with the optically coded paths provided on the outer surface of the rotatably mounted member.

The injection device according to the first aspect of the present invention may further comprise an electronic control circuit operatively coupled to the light sensitive elements. The control circuit may process the electrical signals generated by the light sensitive elements in response to whether or not the light sensitive elements or areas receives reflected light from the highly reflective areas of the optically coded paths. By monitoring the intensity fluctuations of light reflected from the optically coded paths the position of the dose setting member may be determined. The control circuit may be in communication with a display means for displaying the determined setting of the dose setting member and/or display the set dose to be injected from the injection device.

In a second aspect, the present invention relates to a method for determining the position or setting of a dose setting member adapted to set a dose of a medicament to be injected from an injection device, the method comprising the steps of
  projecting a plurality of light beams onto a plurality of optically coded paths provided on an outer surface of a rotatably mounted member, and
  detecting light intensities of a plurality of light beams reflected from the optically coded paths and determining the position or setting of the dose setting member from the detected intensities.

The rotatably mounted member is operatively connected to the dose setting member and is adapted to rotate with the dose setting member. Preferably, the number of light beams equals the number of optically coded paths provided on the rotatably mounted member.

The intensity of the plurality of optical light beams varies in accordance with the position of the dose setting member in that the reflectivity or transparency of the outer surface of the rotatably mounted member varies along the optically coded paths. Preferably, the number of light beams projected onto the outer surface of the rotatably mounted member and the number of light beams reflected thereof is equal to six.

The method according to the second aspect of the present invention may further comprise the step of providing information concerning the detected light intensities to a processing unit, said processing unit being adapted to calculate the position or setting of the dose setting member.

In a third aspect, the present invention relates to an arrangement for determining the position of a dose setting member adapted to set a dose of a medicament to be injected from an injection device, the arrangement comprising a rotatably mounted member having a plurality of optically coded paths arranged on an outer surface thereof, the arrangement further comprising means for generating and guiding a plurality of light beams towards the rotatably mounted member and means for guiding a plurality of light beams from the rotatably mounted member to a plurality of light sensitive elements or areas.

In a fourth aspect, the present invention relates to an arrangement for determining an amount of a medicament injected from an injection device, the arrangement comprising a rotatably mounted member having a plurality of optically coded paths arranged on an outer surface thereof, the arrangement further comprising means for generating and guiding a plurality of light beams towards the rotatably mounted member and means for guiding a plurality of light beams from the rotatably mounted member to a plurality of light sensitive elements or areas.

Thus, according to the fourth aspect of the present invention an arrangement for actually measuring an amount of medicament injected from an injection device is provided. The arrangement according to the fourth aspect may be implemented applying similar means as discussed in connection with the first aspect of the present invention. Thus, the optically coded paths may be provided by varying the optical properties along said paths, such as by varying the optical reflectivity or transparency of the outer surface of the rotatably mounted member. The optical reflectivity or transparency may be varied along the path by positioning strips of metal foil on the outer surface of the rotatably mounted member. Alternatively, the optically coding of the paths may be provided by printing non-reflecting regions on a piece of reflecting tape or other sticky material.

Preferably, the number of guided light beams equals the number of optically coded paths. The plurality of light beams may be generated from a single light source, such as a LED or a laser diode. The light source may emit light in the visible or near infrared region. In order to provide a plurality of light beams the light emitted from the single lights source may be guided into separate channels which guide each of the beams towards an optically coded path. Preferably, the number of light sensitive elements or areas equals the number of optically coded paths.

An electronic control circuit operatively coupled to the light sensitive elements or areas may further be provided. The control circuit may process the electrical signals generated by the light sensitive elements or areas in response to whether or not the light sensitive elements or areas receives reflected light from the highly reflective areas of the optically coded paths. By monitoring the intensity fluctuations of light reflected from the optically coded paths the position of the rotatably mounted member may be determined. The control circuit may be in communication with a display means for displaying an amount of medicament injected from the injection device. The control module may be arranged to display a dose just injected from the injection device and/or it may be arranged to display an accumulated dose injected from the injection device. By accumulated is meant the total volume or total amount of a series of doses injected from the injection device.

BRIEF DESCRIPTION OF THE INVENTION

The present invention will now be explained in further details with reference to the accompanying figures, wherein.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

In its most general aspect the present invention relates to an arrangement adapted for determining the position of a dose setting member of an injection device, such as a pen-type injection device. The medicament to be injected from the injection device can be insulin. The position of the dose setting member is determined by an optically based arrangement where light is either reflected from coded paths arranged on a surface of a rotatably mounted member or transmitted through the coded paths arranged on the surface of the rotatably mounted member.

Figure 1:
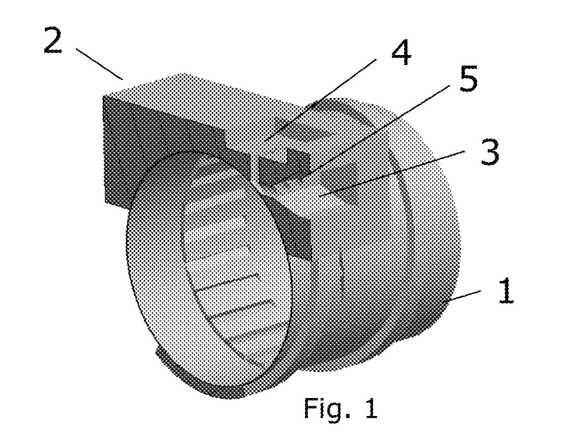
FIG. 1 shows a first embodiment of the present invention.
Figure 2:
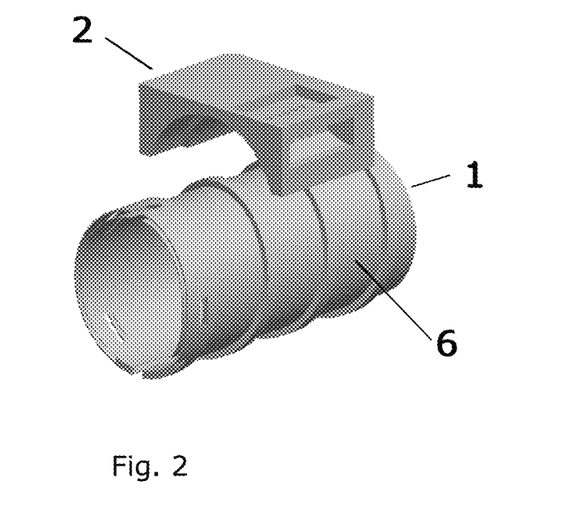
FIG. 2 shows the first embodiment of the present invention wherein the rotatably mounted member is separated from the sensor housing.

A first embodiment of the present invention is depicted in FIG. 1 where a threaded, rotatably mounted member 1 is coupled to a sensor housing 2. The sensor housing 2 has a threaded inner surface adapted to cooperate and engage with the threaded outer surface of the rotatably mounted member 1. Thus, the sensor housing 2 and the rotatably mounted member 1 are coupled via a thread joint—see FIG. 2. The sensor housing 2 has a region 3 adapted to house one or more light sources and a region 4 adapted to house a number of light sensitive elements. Between the regions 3 and 4 a number of light guiding channels 5 exist. Thus, the one or more light sources, such as one or more LEDs or one or more laser diodes, emit light that is guided, via the light guiding channels 5, towards the outer surface of the rotatably mounted member 1. In the embodiment depicted in FIG. 1 the number of light guiding channels 5 is equal to 6. Thus, an LED positioned in region 3 generates 6 light beams which propagate towards the surface of the rotatably mounted member 1. The 6 light beams are incident under an angle of approximately 45 degrees.

The sensor housing 2 keeps the 6 light beams separated so as to avoid cross-talking between the beams. The separation of the light beams also applies to the receiver side of the sensor housing 2, i.e. to the section of the sensor housing 2 that guides light from the rotatably mounted member 1 and to the region 4 adapted to house a number of light sensitive elements. Thus, light beams approaching and leaving the optically coded paths are kept separated in order to avoid cross talk. In the region 4 a photo detector is aligned with each of the light guiding channels guiding light from the rotatably mounted member 1. Thus, in the embodiment depicted in FIG. 1 a sensor array having 6 photosensitive areas is applied. Alternatively, 6 individual photo detectors can be positioned in the region 4.

At the intersection between each of the 6 light beams generated by the light source and the outer surface of the rotatably mounted member an optically coded path is positioned. This optically coded path is a well-defined pattern of optically reflecting and optically absorbing areas arranged along a string or track. The optically coded paths are arranged in the valleys of the rotatably mounted member 1—i.e. in the region denoted 6 in FIG. 2.

Figure 3:
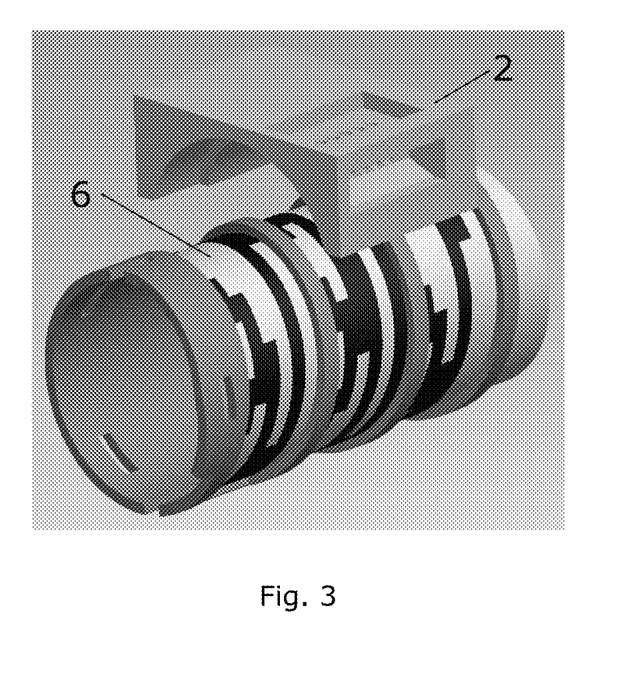
FIG. 3 shows 6 optically coded paths arranged on the surface of the rotatably mounted member.

Evidently, the optically coded paths have a helical shape in that they follow the region 6 of the rotatably mounted member 1. This also implies that the lengths of the optically coded paths exceed a distance longer than the circumference of the rotatably mounted member 1. A rotatably mounted member having 6 optically coded paths arranged thereon is illustrated in FIG. 3. Each path has a width of approximately 1 mm. By having 6 optically coded paths the number of well-defined positions along the length of the entire path equals 64 ($2^6=64$).

The valleys referred to above corresponds to a helically extending recessed track wherein the optical paths are arranged in parallel in the bottom of the recessed track.

An optically coded path is implemented by positioning an aluminium tape on the rotatably mounted member, and positioning, on the aluminium tape, a transparent tape having black or grey areas printed thereon. The black or grey regions act as absorbing areas of the path whereas the aluminium areas (visible through the transparent tape) act as the reflecting areas of the path.

Figure 4:
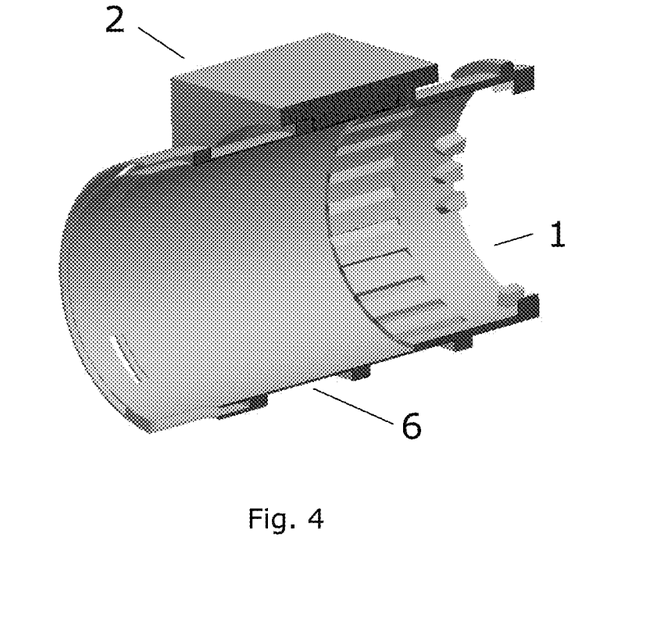
FIG. 4 shows a cross-sectional view of the first embodiment of the present invention.

FIG. 4 shows a cross-sectional view of the rotatably mounted member 1 and the sensor housing 2. As seen the sensor housing 2 abuts the region 6 of the rotatably mounted member 6. The sensor housing 2 is fixed in relation to the injection device whereas the rotatably mounted member 1 is adapted to rotate relative to the injection device when a dose of medicament is to be set. Thus, when setting a dose to be injected the optically coded paths arranged in the region 6 of the rotatably mounted member 1 will pass by an intersection zone where the 6 light beams from the light source hit the rotatably mounted member. This relative movement between the sensor housing 2 and the optically coded paths on the rotatably mounted member 1 will induce intensity fluctuations of the light beams reflected from the paths. For example, if one of the incident light beams hits a highly reflective area a high intensity signal is reflected, whereas if the same incident light beam at another position of the rotatably mounted member 1 relative to the sensor housing 2 hits an absorbing area essentially no signal is reflected. By constantly measuring the reflected signals from all 6 optical paths the combined angular and axial position of the rotatably mounted member, and thereby the position of the dose setting member, can be determined.

Figure 5:
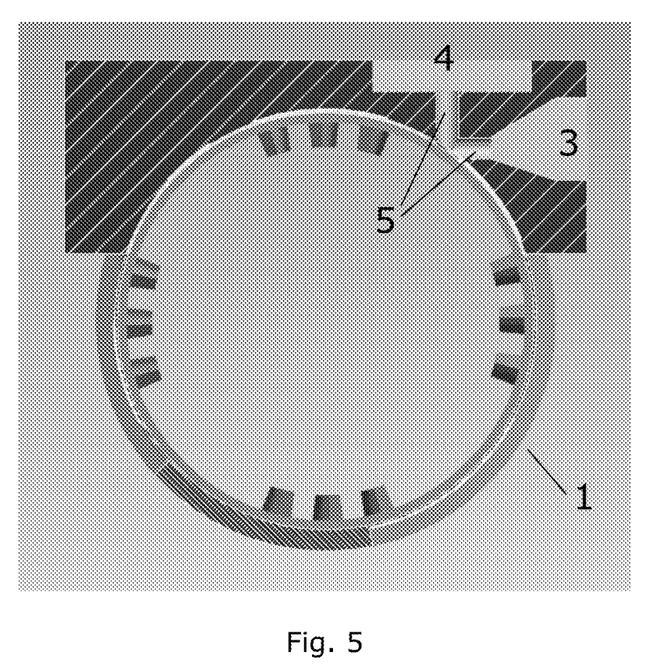
FIG. 5 shows the optical path of a light beam in the first embodiment of the present invention.

The beam path from the light source to the photo detector is depicted in FIG. 5. The light source is positioned in region 3 and light beams propagate in channels 5 toward a detector positioned in region 4. Firstly, light beams generated by the light source propagate in the horizontal part of the channels 5. The beams are redirected into the vertical part of the channels 5 so as to hit the detector in region 4. The redirection of the beams is caused by an interaction of the beams with the surface of the rotatably mounted member 1.

Figure 6:
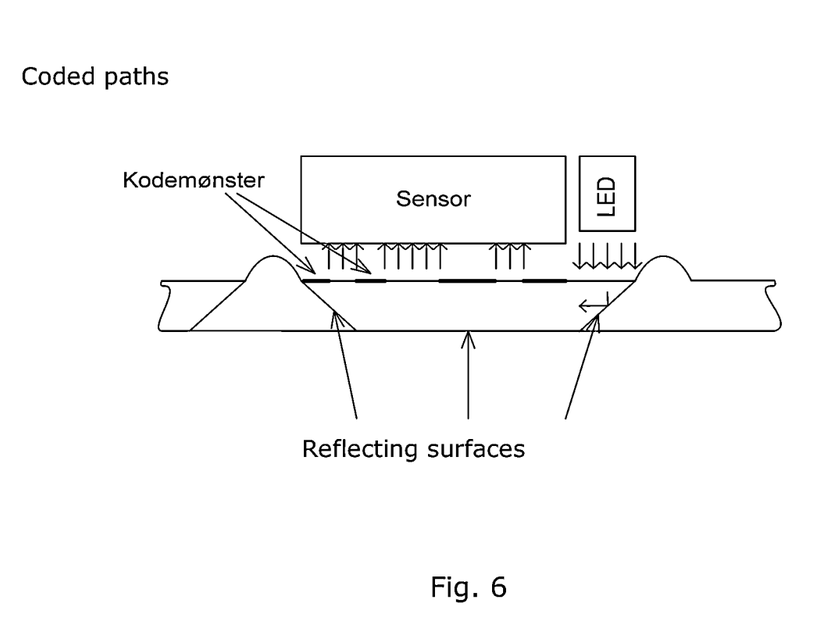
FIG. 6 shows a second embodiment of the present invention.

FIG. 6 shows a second embodiment of the present invention. In this second embodiment the rotatably mounted member is transparent in that it must be capable of guiding light coupled into it. As illustrated in FIG. 6 light from an LED is coupled into the rotatably mounted member where it is guided to the region where optically coded paths are arranged on the surface of the rotatably mounted member. The optically coded paths are arranged by positioning a well-defined pattern of light absorbing elements on the surface of the rotatably mounted member so that light propagating inside the rotatably mounted member is only allowed to escape from the transparent, rotatably mounted member in certain regions along the optically coded paths. The optically coded paths can be arranged as illustrated in FIG. 3. A sensor array having a plurality of light sensitive elements is positioned above the optically coded path so that light escaping the rotatably mounted member can be detected. By detecting the intensity variations caused by a relative movement of the sensor array and the rotatably mounted member the position of this member, and thereby the position of the dose setting member, can be determined.

As already mentioned the 6 optically coded paths allow 64 positions of the dose setting member. Each of these positions correspond a certain amount of medicament, such as insulin. Thus, when the user of the injection device sets a dose to be injected, the user positions the dose setting member at the position that corresponds to the amount of medicament to be injected from the injection device.

The number of optically coded paths arranged on the rotatably mounted member may also be different from 6. For example if the number of well-defined positions required exceeds 64 more than 6 optically coded paths are needed. If only the relative position of the dose setting member is required only 2 optically coded paths are required.

The light source may in principle be any light capable of fitting into the region 3. Obvious choices would be LEDs or laser diodes emitting light in the visible or near infrared regions. The detector for detecting light reflected from optically coded paths can be sensor arrays comprising a plurality light sensitive regions or individual photo detectors. The number of light sensitive areas on a sensor array or the number of individual sensors matches the number of light guiding channels arranged to guide light from the rotatably mounted member and to the detector(s). Similarly, the number of light guiding channels guiding light from the light source and the rotatably mounted member equals the number of light guiding channels arranged to guide light from the rotatably mounted member and to the detector(s).

The invention claimed is:

1. An injection device comprising:
   a dose setting member adapted to set a dose of a medicament to be injected from the injection device,
   a position determining arrangement for determining the amount of a set dose or the amount of an injected dose, the position determining arrangement comprising a rotatably mounted member having at least one optically coded path or track arranged on an outer surface thereof,
   an optic sensor arrangement adapted to sense the optically coded path(s) or track(s), and
   a control circuit coupled to the optic sensor arrangement to determine the position of the rotatably mounted member relative to the optic sensor arrangement,
   wherein the optically coded path(s) or track(s) is/are arranged as helically extending path(s) or track(s) defining a series of information elements on the rotatably mounted member.

2. An injection device according to claim 1, wherein six optically coded tracks are arranged on the outer surface of the rotatably mounted member.

3. An injection device according to claim 1, wherein the information elements extend along the helical track around more than one complete revolution of the rotatably mounted member.

4. An injection device according to claim 1, wherein the rotatably mounted member is coupled to a sensor housing.

5. An injection device according to claim 1, wherein the optically coded track(s) are provided by varying the optical properties along said track(s).

6. An injection device according to claim 5, wherein the optical properties along the track(s) are varied by varying the optical reflectivity or transparency of the outer surface of the rotatably mounted member.

7. An injection device according to claim 1, wherein the rotatably mounted member is at least partly transparent.

8. An injection device according to claim 7, further comprising light emitting structure adapted to emit a beam of light into the rotatably mounted member.

9. An injection device according to claim 8, further comprising light detecting structure having a plurality of light sensitive areas, the light detecting structure being arranged to detect light escaping the outer surface of the rotatably mounted member.

10. An injection device according to claim 9, wherein the number of light sensitive areas equals the number of optically coded path(s) or track(s).

11. An injection device according to claim 1, further comprising structure for guiding a plurality of guided light beams, each light beam being guided so as to be incident on one optically coded track.

12. An injection device according to claim 11, wherein the number of guided light beams equals the number of optically coded tracks.

13. An injection device according to claim 11, wherein the optic sensor arrangement comprise a plurality of light sensitive elements.

14. An injection device according to claim 13, wherein the number of light sensitive elements equals the number of optically coded tracks.

15. An injection device according to claim 13, further comprising structure for guiding a plurality of light beams reflected from the optically coded path(s) or track(s) to the light sensitive elements.

16. An injection device according to claim 11, wherein the light guiding structure arranged to provide light beams to and from the optically coded path(s) or track(s) are arranged as through-going openings in a housing.

17. An injection device according to claim 16, wherein the light guiding structure for guiding light to the optically coded path(s) or track(s) are arranged so that the light beams are incident onto the optically coded path(s) or track(s) under an angle of 40-50 degrees.

18. An injection device according to claim 16, wherein the light guiding structure for guiding light from the optically coded path(s) or track(s) to the light sensitive elements are arranged so that the light beams leave the optically coded path(s) or track(s) under an angle of 40-50 degrees.

* * * * *